(12) United States Patent
Bregulla et al.

(10) Patent No.: US 8,784,477 B2
(45) Date of Patent: Jul. 22, 2014

(54) STENT GRAFT WITH TWO LAYER EPTFE LAYER SYSTEM WITH HIGH PLASTICITY AND HIGH RIGIDITY

(75) Inventors: Rainer Bregulla, Balingen (DE); Gunther Stockert, Ursrainer Ring (DE)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 218 days.

(21) Appl. No.: 12/985,151

(22) Filed: Jan. 5, 2011

(65) Prior Publication Data
US 2012/0172977 A1 Jul. 5, 2012

(51) Int. Cl.
| | | |
|---|---|---|
| *A61F 2/82* | (2013.01) | |
| *A61L 31/14* | (2006.01) | |
| *A61L 27/36* | (2006.01) | |
| *A61L 31/04* | (2006.01) | |
| *A61F 2/915* | (2013.01) | |
| *A61F 2/07* | (2013.01) | |

(52) U.S. Cl.
CPC ......... *A61L 27/3683* (2013.01); *A61L 2400/16* (2013.01); *A61F 2002/91575* (2013.01); *A61F 2002/072* (2013.01); *A61L 31/14* (2013.01); *A61F 2/915* (2013.01); *A61L 31/048* (2013.01); *A61F 2/07* (2013.01)
USPC .......................... 623/1.44; 623/1.13; 623/1.49

(58) Field of Classification Search
CPC ................ A61F 2/07; A61F 2002/072; A61F 2002/075; A61F 2/856; A61F 2210/0076; A61F 2250/0018
USPC ............... 623/1.1, 1.13, 1.15, 1.16, 1.18–1.2, 623/1.23, 1.27, 1.32, 1.44, 1.49, 23.7, 23.71
See application file for complete search history.

(56) References Cited

U.S. PATENT DOCUMENTS

| | | | | |
|---|---|---|---|---|
| 5,217,666 A | * | 6/1993 | Tamaru et al. | 264/112 |
| 5,628,788 A | * | 5/1997 | Pinchuk | 623/1.2 |
| 5,667,523 A | * | 9/1997 | Bynon et al. | 623/1.13 |
| 5,916,264 A | * | 6/1999 | Von Oepen et al. | 623/1.15 |
| 5,931,865 A | * | 8/1999 | Silverman et al. | 138/103 |
| 6,027,779 A | * | 2/2000 | Campbell et al. | 428/36.91 |

(Continued)

FOREIGN PATENT DOCUMENTS

| | | |
|---|---|---|
| EP | 0878173 A1 | 11/1998 |
| JP | 06343688 A | 12/1994 |

(Continued)

OTHER PUBLICATIONS

International Search Report issued by the European Patent Office on Apr. 13, 2012 in the corresponding International Patent Application No. PCT/US2011/067595.

*Primary Examiner* — David Isabella
*Assistant Examiner* — Suba Ganesan
(74) *Attorney, Agent, or Firm* — Jonathan D. Feuchtwang; Fulwider Patton LLP

(57) ABSTRACT

A vascular prosthesis and method are disclosed comprising a first flexible stent having a lattice structure with a compacted configuration and an expanded configuration, a second flexible stent inside the first flexible stent to form a tubular structure, a first film layer of graft material such as expanded polytetrafluoroethylene sandwiched between the first and second flexible stents, and a second film layer of expanded polytetrafluoroethylene sandwiched between the first and second flexible stents, the second layer having a higher rigidity and a lower plasticity than the first layer.

7 Claims, 3 Drawing Sheets

(56) References Cited

U.S. PATENT DOCUMENTS

| | | | |
|---|---|---|---|
| 6,099,559 A * | 8/2000 | Nolting | 623/1.16 |
| 6,428,571 B1 * | 8/2002 | Lentz et al. | 623/1.4 |
| 7,083,822 B2 * | 8/2006 | Brightbill | 427/2.25 |
| 2004/0176833 A1 * | 9/2004 | Pavcnik et al. | 623/1.13 |
| 2005/0209679 A1 * | 9/2005 | Melsheimer | 623/1.15 |

FOREIGN PATENT DOCUMENTS

| | | |
|---|---|---|
| WO | 9633672 A1 | 10/1996 |
| WO | 9800090 A2 | 6/1997 |
| WO | 9947077 A1 | 9/1999 |
| WO | 0101887 A1 | 1/2001 |

* cited by examiner

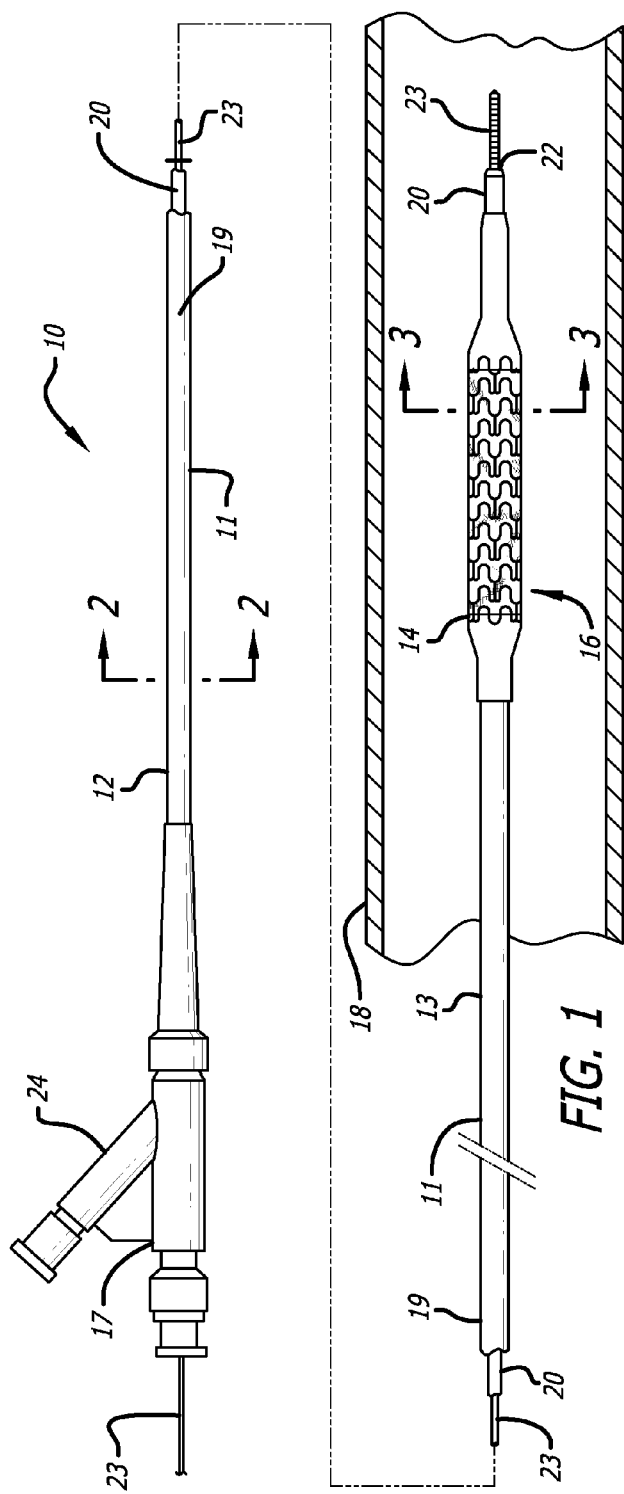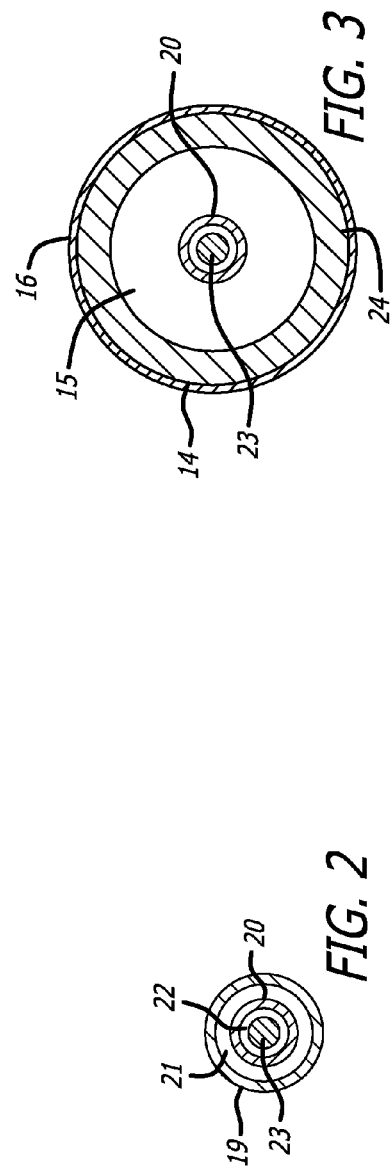

STENT GRAFT WITH TWO LAYER EPTFE LAYER SYSTEM WITH HIGH PLASTICITY AND HIGH RIGIDITY

BACKGROUND

The present invention relates generally to an implantable prosthesis used to repair or replace a body lumen. More particularly, the present invention relates to an endoluminal prosthesis or stent graft having at least two ePTFE layers sandwiched between first and second stents with one ePTFE layer having higher plasticity and one layer having higher rigidity to lower the sensitivity to hole formation.

BACKGROUND OF THE INVENTION

Endoluminal prostheses are medical devices used in the treatment of diseased or occluded blood vessels and other body lumens by repairing, replacing, or supporting the tissue. The prosthesis may be used to treat a wide variety of diseases and injuries such as stenosis of the vessel, thrombosis, occlusion, and aneurysm. One type of endoluminal prosthesis used in the repair of diseases in various body vessels is a stent. A stent is a generally longitudinal tubular device formed of biocompatible material that is used to open and support various lumens in the body. Endovascular stents have become widely used for the treatment of stenosis, strictures, and aneurysms in various blood vessels. These devices are implanted within the vessel to keep open or reinforce collapsing or partially occluded sections of the vessel.

Stents generally comprise a collapsible, flexible lattice structure formed of a metallic material. This structure allows the stent to be radially compressed onto a catheter, for example, for intraluminal implantation. Once properly positioned adjacent to the damaged vessel, the stent is radially expanded to support and reinforce the vessel, allowing blood to flow through the stent's tubular configuration. Radial expansion of the stent may be accomplished by the outward pressure of an inflating balloon as part of the catheter, or the stent may be of the self-expanding variety, such as those constructed of nitinol, that may be enclosed in a protective sheath and radially expanded as the sheath is withdrawn.

A graft is another type of endoluminal prosthesis that is used to repair and replace various body vessels. Whereas a stent provides structural support to hold a damaged vessel open, a graft provides an artificial lumen. Grafts are tubular devices which may be formed of a variety of material, including textiles, and non-textile materials. One type of non-textile material particularly suitable for use as an implantable prosthesis is polytetrafluoroethylene (PTFE). PTFE exhibits superior biocompatibility and low thrombogenicity, which makes it particularly useful as vascular graft material in the repair or replacement of blood vessels. In vascular applications, some grafts are manufactured from expanded PTFE (ePTFE) tubes. These tubes have a microporous structure that allow natural tissue in growth and cell endothelization once implanted in the vascular system. This contributes to long term healing and patency of the graft.

A stent and a graft may be formed into a stent-graft endoprosthesis to combine the features and advantages of each separate device. For example, tubular coverings have been provided on the inner and/or outer surfaces of stents to form one type of stent-graft. It is often desirable to incorporate a thin-walled graft in the stent-graft endoprosthesis to minimize the profile of the endoprosthesis and to maximize the flow of blood through the endoprosthesis.

Sheets or films of ePTFE have commonly been used in conjunction with stents. For example, U.S. Pat. Nos. 5,700,285 and 5,735,892 to Myers et al. describe overlapping a sheet of ePTFE onto a stent to form a tubular graft. The graft is secured to the stent by an application of thermoplastic adhesive and heat treatment to melt the adhesive. A seam, which is formed where the sheet overlaps, is also sealed through the use of the thermoplastic adhesive. U.S. Pat. No. 6,361,637 to Martin et al. describes the securement or interweaving of ePTFE graft strips through helical windings of an undulating stent wire. The ePTFE strips are spaced apart from the apices of the undulating wire such that no strip completely covers a winding of the undulating wire. The graft strips are secured to the stent wire by use of a thermoplastic adhesive and the application of heat.

U.S. Pat. No. 6,344,054 to Parodi describes a stent graft having its graft being secured to only one end of the stent. Such a graft avoids undue stresses being placed on the graft during contraction and expansion of the stent by only securing one end of the graft to the stent. U.S. Patent Application Publication No. 2003/0220682 to Kujawski describes a hybrid braided stent having a plurality of overlapping graft segments. The graft segments are described as being textile graft segments made by, for example, braiding yarns. One end of a graft segment is secured to the stent, and the other end of the graft segment overlaps an adjacent secured graft segment.

Furthermore, ePTFE surfaces have been modified to alter porosity. For example, U.S. Pat. No. 5,466,509 to Kowligi et al. described a more porous ePTFE which is obtained by impressing a pattern, into extruded PTFE and then expanding the PTFE. The pattern is described as being impressed by knurling or rolling a sheet of PTFE sheet between rollers having a pattern formed on the surface of the roller. A roller with a coarse pattern is described as producing a wider distribution of internodal distances of the ePTFE as compared to a finer pattern, thereby increasing the porosity of the ePTFE material.

U.S. Pat. No. 5,462,781 to Zukowski describes an implantable porous expanded polytetrafluoroethylene material having a microstructure of nodes interconnected by fibrils where its surface has been modified by the removal of fibrils so that under magnification the surface has the appearance of freestanding node portions not interconnected by fibrils but rather having open valleys disposed between the freestanding node portions. Unmodified material beneath the surface is described as maintaining the original microstructure of nodes interconnected by fibrils. The modification is described as being done by exposing the surface to radio frequency gas plasma discharge with a reactive etching gas. The modified surface is described as having increased hydrophobicity. Such a modified surface is described as having improved blood contact properties and tissue in growth characteristics useful as an implantable device, such as a breast prosthesis.

Expanded polytetrafluoroethylene stent grafts are typically subject to plastic deformation, especially when compressing the stent-graft for loading into the delivery system, delivering the stent-graft through a highly tortuous bodily lumen, and during placement/deployment at the target implant site. Such plastic deformation may lead to the tearing or puncturing of the ePTFE, leaving the stent-graft endoprosthesis prone to leakage of blood therethrough. Furthermore, plastic deformation of expanded polytetrafluoroethylene grafts may lead to physical deformities in the graft, such as buckling, which is also undesirable because it may lead to poor blood flow patterns. A tear or puncture is particularly susceptible when crimping the stent graft onto the balloon for delivery, in which case there is no method for determining if the graft is intact, leading to the possibility that a torn or punctured graft could hinder performance of the overall device. This problem is exacerbated by stent geometries that are becoming smaller and smaller, leading to the ePTFE layer being squeezed too much between the thin struts during the crimping and embedding process. That is, a high point load on the ePTFE film or foil can directly lead to puncturing. The present invention recognizes this problem, and solves the issue with a novel solution to overcome leakage in the event of a stent graft puncture.

SUMMARY OF THE INVENTION

The present invention addresses the problem above by utilizing a two layer system of ePTFE graft materials sandwiched between inner and outer stent structures. One ePTFE layer or tube provides a higher plasticity and the second layer provides higher rigidity. The sequence of the different layers can be either to take the high plasticity layer as the inner layer and to take the high rigidity layer as the outer layer, or vice versa. The layer system of one high plasticity and one high rigidity provides enhanced resistance to hole formation in the graft. Moreover, as the two ePTFE tubes expand upon deployment, any small hole that is initially coincident in the layers when in the compressed configuration will, upon expansion of the tubes, occupy two different circumferential positions relative to each other. The relative movement of the two layers will help self-seal any small holes formed during the crimping process.

BRIEF DESCRIPTION OF THE DRAWINGS

FIG. 1 is an elevated view partially in section of a balloon catheter of the present invention;

FIG. 2 is a transverse cross sectional view of the balloon catheter of FIG. 1 taken along lines 2-2;

FIG. 3 is a transverse cross sectional view of the balloon catheter of FIG. 1 taken along lines 3-3;

DETAILED DESCRIPTION OF THE PREFERRED EMBODIMENTS

Figure 4:
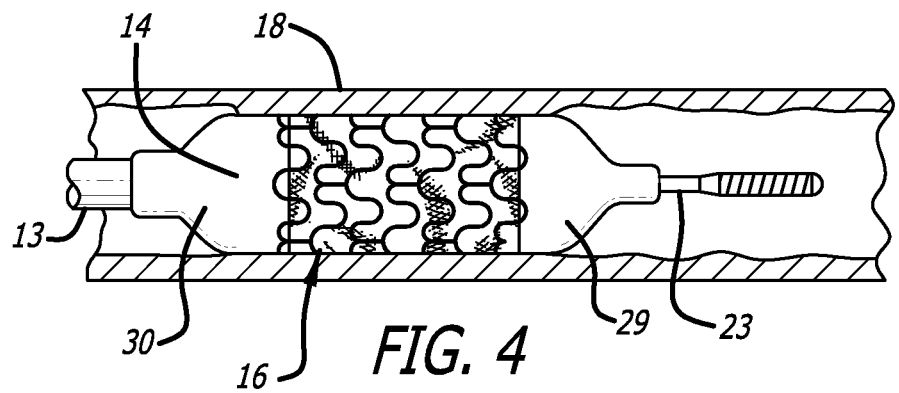
FIG. 4 is an enlarged view of the balloon catheter of FIG. 1 with a vascular stent mounted thereon.

FIG. 1 shows a balloon catheter that can be used to illustrate the features of the invention. The catheter 10 of the invention generally comprises an elongated catheter shaft 11 having a proximal section 12, a distal section 13, an inflatable balloon 14 on the distal section 13 of the catheter shaft 11, and an adapter 17 mounted on the proximal section 12 of shaft 11. In FIG. 1, the catheter 10 is illustrated within a greatly enlarged view of a patient's body lumen 18, prior to expansion of the balloon 14.

The catheter shaft 11 has an outer tubular member 19 and an inner tubular member 20 disposed within the outer tubular member and defining, with the outer tubular member, inflation lumen 21. Inflation lumen 21 is in fluid communication with the interior chamber 15 of the inflatable balloon 14. The inner tubular member 20 has an inner lumen 22 extending therein which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19.

FIGS. 2 and 3 show transverse cross sections of the catheter shaft 11 and balloon 14, respectively, illustrating the guidewire receiving lumen 22 of the guidewire's inner tubular member 20 and inflation lumen 21 leading to the balloon interior 15. The balloon 14 can be inflated by a fluid such as air, saline, or other fluid that is introduced at the port in the side arm 25 into inflation lumen 21 contained in the catheter shaft 11, or by other means, such as from a passageway formed between the outside of the catheter shaft 11 and the member forming the balloon 14, depending on the particular design of the catheter. The details and mechanics of the mode of inflating the balloon vary according to the specific design of the catheter, and are omitted from the present discussion.

Figure 5:
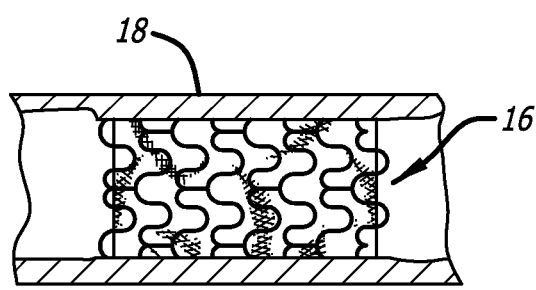
FIG. 5 is an enlarged view of the stent of FIG. 4 disposed in a patient's vascular after removal of the balloon.

In a typical procedure to implant a stent graft 16, the guide wire 23 is advanced through the patient's vascular system by well known methods so that the distal end of the guide wire is advanced past the location for the placement of the stent in the body lumen 18. Prior to implanting the stent graft 16, the cardiologist may wish to perform an angioplasty procedure or other procedure (i.e., atherectomy) in order to open the vessel and remodel the diseased area. Thereafter, the stent graft delivery catheter assembly 10 is advanced over the guide wire 23 so that the stent graft 16 is positioned in the target area. The balloon 14 is inflated so that it expands radially outwardly and in turn expands the stent graft 16 radially outwardly until the stent graft 16 bears against the vessel wall of the body lumen 18. The balloon 14 is then deflated and the catheter withdrawn from the patient's vascular system, leaving the stent graft 16 in place to dilate the body lumen. The guide wire 23 is typically left in the lumen for any post-dilatation procedures, and subsequently is withdrawn from the patient's vascular system. As depicted in FIG. 4, the balloon 14 is fully inflated with the stent graft 16 expanded and pressed against the vessel wall, and in FIG. 5, the implanted stent graft 16 remains in the vessel after the balloon has been deflated and the catheter assembly and guide wire have been withdrawn from the patient. As noted above, there are also self-expanding prostheses where the stents are made out of a shape-memory material such as nitinol, formed so as to undertake the expanded configuration in the unconstrained environment. To implant this type of device, a sheath is used in place of the balloon to constrain the stent while the device is delivered to the body lumen. Once the device is properly placed, the sheath is withdrawn allowing the stent to expand against the vessel wall and assume its position in the vessel. The present invention is intended to include both self-expanding prostheses as well as those that are expanded by mechanical or other means.

The stent graft 16 of the present invention uses two layers of ePTFE sandwiched between an inner stent 40 and an outer stent 42. One of the layers of ePTFE material is formed so as to have a high plasticity, making it more resistant to punctures, and a second layer of ePTFE of is formed to have a high rigidity, for strength of the stent graft. The two layers 46,48 work to provide a better balance of flexibility and strength as compared with other stent grafts. The layers 46,48 also provide better protection against puncture due to contrast between the two materials. In addition, the two layers will expand differently which, as explained below, can alleviate the effects of a puncture should one occur in the stent graph.

Figure 7:
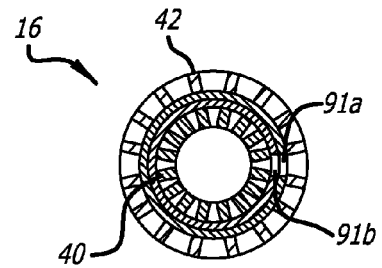
FIG. 7 is a cross-sectional view of the stent graft of FIG. 6.

The procedure for creating the stent graft is to place a tube 48 of ePTFE having a high plasticity over a second tube 46 of ePTFE having a high rigidity (the order of these two layers can be reversed as well) to create a double layer tubing of ePTFE foil (see FIG. 7). The double layer of ePTFE film or foil is then placed over the exterior of the inner stent member 40. Then, the outer stent 42 is placed over the double ePTFE layer to sandwich the double ePTFE layer between the inner and outer stents. The inner and outer stents are welded together, such as at the ends, as is known in the art, to sandwich the ePTFE layers 46,48 therebetween. This stent graft 16 can then be mounted on a balloon catheter such as that shown in FIG. 1 for deployment in the patient.

Figure 6:
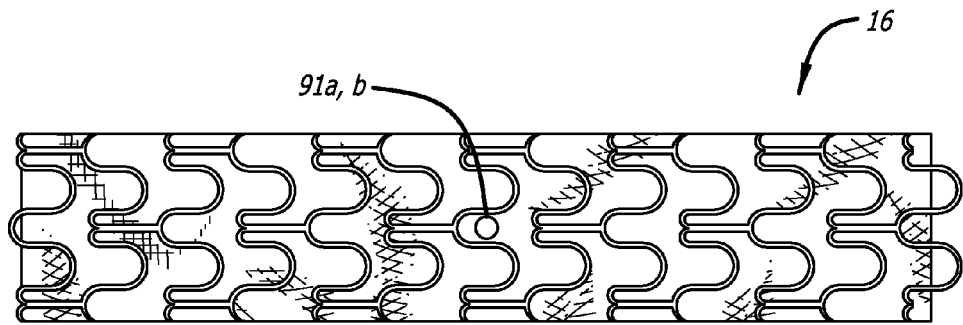
FIG. 6. is an enlarged, side view of the stent graft illustrating a hole due to crimping.

FIG. 6 illustrates an enlarged view of the stent graft 16 in its compacted state as it would be found on the balloon, where the balloon has been omitted. The stent graft 16 of FIG. 6 is shown as it would appear crimped on a balloon, and FIG. 7 is a cross-sectional view of the stent graft 16 of FIG. 6, which shows holes 91a, b aligned and coincident in each ePTFE layer, respectively, also passing through the inner and outer stent walls. This is similar to what would occur if there were to be a puncture during the crimping processes of securing the stent graft to the balloon. The holes 91a,b as may occur during the crimping process, the welding process, or in the handling or manufacturing processes. When in the crimped state, the holes passes through both layers 46,48 of the ePTFE and are aligned so that they appear as a single hole. Without the two layers of ePTFE of the present invention, when expanded these holes 91a.b could present a risk of blood leakage or other structural deformities of the stent graft.

Figure 8:
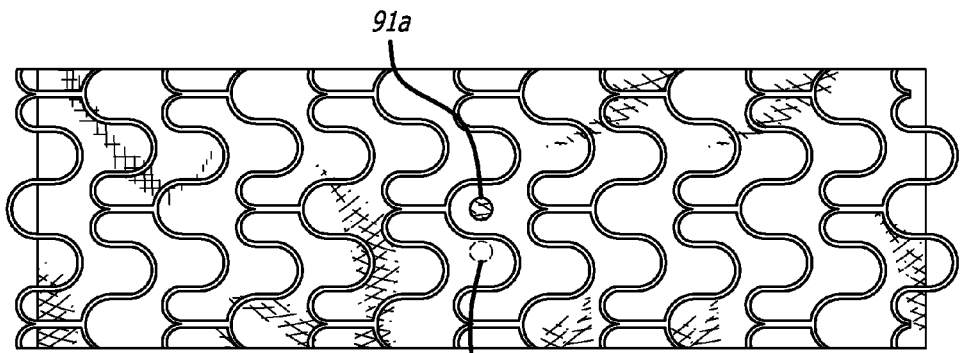
FIG. 8 is an enlarged, side view of the stent graft of FIG. 6 after expansion, partially in shadow, illustrating the relative movement of the two holes.
Figure 9:
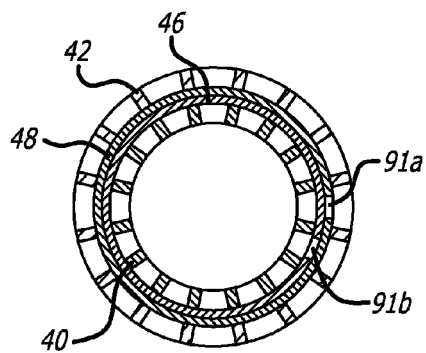
FIG. 9 is a cross-sectional view of the stent graft of FIG. 8.

FIG. 8 depicts the same stent graft after expansion, and FIG. 9 shows the expanded stent graft in cross section. When the stent graft 16 is expanded, as for example by a balloon or a self-expanding nitinol stent configuration, the inner and outer ePTFE layers (46, 48 respectively) of the present invention expand in slightly different geometries due to the differences in their material properties. As a result, the holes 91a,b that originally were aligned are now misaligned so that there is no overlap, and each layer blocks the hole in the adjacent layer. That is, hole 91a from the outer layer 48 moves to a different circumferential position when compared with the hole 91b of the inner layer 46, best shown in FIG. 9. This misalignment of the holes 91a,b provides protection against leakage from holes developed during the crimping process, and operates to self-seal the stent graft should a hole occur.

The relative movement of the two ePTFE layers provides a defense against leaks, and also contributes to the overall integrity of the stent graft. That is, the two layers provide a back-up to each other in the event one layer has a defect or if one layer is punctured during the manufacturing process. The properties of the ePTFE materials can be adjusted and manipulated using different sintering processes. For example, the layer to have the higher rigidity could be sintered at a higher level than the layer that is to have the higher plasticity, which would be sintered at a lower level. Other manufacturing processes could be used to alter the properties of the ePTFE film so that one layer would have a higher rigidity and one layer would have a higher plasticity.

While particular forms of the invention have been illustrated and described, it will be apparent to those skilled in the art that various modifications can be made without departing from the spirit and scope of the invention. Accordingly, it is not intended that the invention be limited except by the appended claims.

We claim:

1. A vascular prosthesis comprising:
    a first flexible stent having a lattice structure with a compacted configuration and an expanded configuration;
    a second flexible stent inside the first flexible stent to form a tubular structure, the second flexible stent having a lattice structure with a compacted configuration and an expanded configuration;
    a first film layer of expanded polytetrafluoroethylene sandwiched between the first and second flexible stents; and
    a second film layer of expanded polytetrafluoroethylene sandwiched between the first and second flexible stents, the second layer having a higher rigidity and a lower plasticity than the first layer, wherein the first film layer and second film layer are circumferentially positioned from each other in a first circumferential position when the first and second flexible stents are in the compacted configuration and are circumferentially positioned from each other in a second circumferential position which is different from the first circumferential position when the first and second flexible stents are in the expanded configuration.

2. The vascular prosthesis of claim 1, wherein the first film layer is sintered at a lower level than the second film layer.

3. The vascular prosthesis of claim 1, wherein the first film layer expands to a different circumferential position than a circumferential position of the second film layer when the first and second flexible stents are expanded to their expanded configuration.

4. A method for making a vascular prosthesis comprising:
    providing a first expandable, tubular stent;
    forming a multi-layer graft member by applying a first tubular member of ePTFE on a mandrel, and then applying a second tubular member of ePTFE onto the first tubular member, the first tubular member being movable circumferentially relative to the second tubular member, wherein the second tubular member of ePTFE has a different rigidity and plasticity than the first tubular member;
    placing the multi-layer graft member on the first expandable, tubular stent;
    placing a second expandable tubular stent over the multi-layer graft member to sandwich the multi-layer tubular graft member between the first and second stents; and
    affixing the first expandable tubular stent to the second expandable tubular stent.

5. The method of making a vascular prosthesis of claim 4, further comprising a step of forming the first tubular member of ePTFE with a different sintering level than the second tubular member of ePTFE.

6. The method of making a vascular prosthesis of claim 4, further comprising the step of forming the first and second tubular stents out of a shape memory material.

7. The method of claim 4, wherein the vascular prosthesis is adapted to be crimped onto a catheter balloon.

* * * * *